United States Patent [19]

Albertini

[11] Patent Number: 5,112,735
[45] Date of Patent: May 12, 1992

[54] DETECTION OF LYMPHOCYTE AMPLIFICATION

[75] Inventor: Richard J. Albertini, Underhill Center, Vt.

[73] Assignee: University of Vermont, Burlington, Vt.

[21] Appl. No.: 337,400

[22] Filed: Apr. 13, 1989

Related U.S. Application Data

[63] Continuation-in-part of Ser. No. 65,357, Jun. 22, 1987, abandoned.

[51] Int. Cl.$^5$ .................. C12Q 1/68; G01N 33/53; G01N 33/566; G01N 33/48
[52] U.S. Cl. .................................. 435/6; 435/7.1; 435/240.1; 435/240.2; 436/501; 436/506; 436/63; 436/94; 935/77; 935/78
[58] Field of Search ............... 435/6, 7, 240.1, 240.25, 435/948; 436/63, 506, 543; 935/77, 78

[56] References Cited

U.S. PATENT DOCUMENTS

| | | | |
|---|---|---|---|
| 4,066,510 | 1/1978 | Thilly | 435/6 |
| 4,544,632 | 10/1985 | Yamamura et al. | 435/948 |
| 4,647,535 | 3/1987 | Ritts, Jr. | 435/948 |

OTHER PUBLICATIONS

Abertini et al., (1982) PNAS, U.S.A. 79:6617-6621.
Yanagi et al., (1984) Nature, 308:145-149.
Yang et al., (1984) Nature, 310:412-414.
Albertini et al., (1985) Nature, 316:369-371.
Nicklas, J., O'Neill, Patrick, and Albertini, Richard J. 1986, Use of T-Cell Receptor Gene Probes to Qualify the in Vivo Hprt Mutations in Human T-Lymphocytes, Mutation Res. 173:67-72.

*Primary Examiner*—Robert A. Wax
*Assistant Examiner*—Stephanie W. Zitomer
*Attorney, Agent, or Firm*—Pretty Schroeder Brueggemann & Clark

[57] ABSTRACT

A method for detecting lymphocyte clonal amplification in a mammal by cloning of lymphocytes so as to identify cell lines expressing a mutation at a structural locus and determining the structure of the antigen receptor in the mutated clonal cell lines. Similar rearrangements of the regions of nucleic acid encoding antigen receptor among multiple isolated clones from a single individual indicate an in vivo clonal lymphocyte amplification event.

15 Claims, No Drawings

DETECTION OF LYMPHOCYTE AMPLIFICATION

This application is a continuation-in-part of United States patent application Ser. No. 065,357, filed Jun. 22, 1987, now aband. the entire specification of which is incorporated herein by reference.

BACKGROUND OF THE INVENTION

The invention relates generally to cells of the immune system and more specifically to clonal amplification of lymphocytes.

Higher animals are distinguished by the presence of an immune system which serves to recognize and respond to foreign materials, or antigens, invading the organism. These functions are carried out by cells called lymphocytes which exist in two classes, B lymphocytes or B-cells and T lymphocytes or T-cell. When activated by an antigen, B-cells differentiate and secrete antibodies, or immunoglobulins, which recognize and bind to foreign substances. Activated T-cells perform a variety of functions including assisting particular B-cells and initiating reactions to eliminate the antigen.

Individual B-cells and T-cells are both highly specific to particular antigens. Each B-cell produces a single homogeneous antibody species, distinguished by the amino acid sequence of its peptide chains, which can bind to only a very limited array of antigens. T-cells derive their specificity from the structure of antibody-like molecules located on their surfaces, termed T-cell receptors, or TCRs, which also recognize and bind a limited array antigens.

Mammals typically possess 100,000 to 100,000,000 lymphocytes of different specificities, collectively capable of responding to a vast range of antigens. Most lymphocytes in human peripheral blood are nondividing. Some, however, are dividing because mature antigen-reactive T-cells and B-cells periodically undergo clonal amplification whereby a cell having specificity for a particular antigen divides repeatedly to provide a large number of identical cells or clones. Clonal amplification of lymphocytes can occur in response to specific antigens or other stimuli. Antigenic stimuli may derive from external stimuli such as infectious agents or organ transplants, or from endogenous stimuli such as tissue antigens in autoimmune diseases or neoantigens in cancer. By generating large numbers of immunologically reactive cells, this clonal amplification may either benefit the host, by promoting resistance to infection or rejection of tumors, or may in fact harm the host, by causing autoimmune diseases or the rejection of organ transplants. Clonal amplification can also occur in lymphomas, such as leukemia, where malignant lymphocytes divide repeatedly.

T-lymphocytes acquire their unique antigen specificity early in the life of the individual as they differentiate in the thymus. Antibodies and TCRs are composed of multiple peptide chains: the heavy and light chains in antibodies and the $\alpha$, $\beta$, etc., chains in the TCRs, all encoded by the corresponding genes. Within each of these genes are multiple related nucleotide sequences encoding the so-called variable (V), constant (C), diversity (D) and joining (J) regions. During maturation of the lymphocytes, these DNA regions are separately rearranged in each cell to give a particular combination of C and V, D and J regions and confer the uniqueness of the antigen specific receptors found in mature reactive T- and B- cells. Each gene rearranges independently in a cell to yield a great potential diversity of specific antigen reactive cells marked by a like diversity of TCR gene DNA restriction fragment patterns. There may be 25 to 50 copies of the V region, and several copies of each of the other regions, providing some millions of possible unique rearrangements. Once rearranged, the gene patterns remain throughout the life of the mature lymphocyte and in all of its clonal descendants. Because these cells presumably persist for many years, the patterns endure for the life of the individual.

The ability to recognize lymphocyte clonal amplification in vivo would have enormous diagnostic and therapeutic benefits. For example, the early diagnosis of premalignancy is often crucial for implementing effective therapy. Identifying a clonal amplification, even one resulting in a vast number of clonal cells, is particularly difficult because of the large potential diversity of unique antigen sensitive cells. A large clonal amplification is merely a needle in the haystack within the vast repertoire of antigen-sensitive cells. A method that would selectively direct attention to those lymphocytes that are actively dividing or have recently divided in vivo, would greatly facilitate such identification. The present invention satisfies these needs and provides related advantages as well.

SUMMARY OF THE INVENTION

The present invention provides a unique and sensitive method for detecting the presence of a clonal lymphocyte amplification event in a mammal. By focusing on lymphocytes exhibiting somatic cell mutations, the method promotes detection of lymphocyte cell populations which have undergone clonal amplification, as recognized by similarity of the TCRs. Moreover, the invention provides a method for identifying lymphocytes involved in a lymphocyte mediated pathologic state or ascertaining the antigen to which lymphocyte clones are reactive.

According to the method, a sample of lymphocytes is cloned in the presence of an agent indicative of a prior mutation event to provide cloned cell populations. Those cloned cell populations indicated to have had a prior mutation event are then selected and separately grown to provide isolated mutated cloned cell populations. The arrangement of regions of nucleic acid coding for specific antigen receptors are determined and compared; similarity of such arrangements indicates clonal amplification of lymphocytes derived from a common parental cell. Determination of clonal amplification is useful in the diagnosis of certain disease states.

In another embodiment, a sample of lymphocytes is cloned in the presence of an agent indicative of a prior mutation event. Those cloned cell populations indicated to have had a prior mutation event are then selected and separately grown to provide isolated mutated cloned cell populations. These isolated mutated cloned cell populations are then tested for reactivity to antigens suspected of causing said lymphocyte mediated pathologic state. Such a procedure is useful to identify lymphocytes involved in such a lymphocyte mediated pathologic state and to identify antigens causing such a state.

It will be apparent from the foregoing that the present invention provides a novel method for detecting clonal lymphocyte amplifications. Other features and advantages of the present invention will become apparent from the more detailed description which illustrates, by way of example, the principles of the invention.

DETAILED DESCRIPTION OF THE INVENTION

In accordance with the invention, there is provided a method of detecting lymphocyte clonal amplification. Repeated divisions of cells derived from a single parent lymphocyte result in numerous identical cells or clones. That these lymphocyte clones are derived from a common parental cell is evidenced by the commonality of their specific antigen receptors, antibodies in B-cells and TCRs in T-cells. The amino acid sequence of a TCR peptide, for example, renders it specific to a particular and limited array of antigens. In any individual there are a vast variety of TCR types estimated at $10^6$ to $10^7$. The variety of TCR specifities results from rearrangements of the regions of the nucleic acid encoding the TCR peptides. The genes encoding the TCR peptides comprise several different regions, including those termed V, C, D and J. During maturation in the thymus, each T-lymphocyte differentiates to synthesize only a single molecular species of TCR. While not wishing to be bound by this explanation, it is believed that translocations or rearrangements of the DNA of the V, C, D and J regions is the mechanism by which a T-lymphocyte is committed to expressing a single TCR.

Analogously, each B-cell exclusively produces a single homogeneous species of antibody, or immunoglobulin, molecule. This specificity is thought to result during maturation from rearrangement of various regions of the DNA encoding the immunoglobulin peptides. For the purposes of the present invention, such rearrangement events in T-cells and B-cells are not considered to be "mutations", as the term is used herein.

Somatic gene mutations result when there is an alteration of the nucleotide sequence of a gene encoding a peptide. Such change may include a substitution of one nucleotide for another, or the insertion or deletion of one or more nucleotides, resulting in a change in the corresponding amino acid sequence of the encoded peptide. Somatic gene mutations are distributed largely stochastically in that, with some exceptions, they are distributed at random among the genes of the genome. However, mutations are more likely to occur in cells which are undergoing mitosis, or cell division, because they often result from inaccurate DNA replication. Thus, a cell lineage which has undergone repeated divisions, as is the case in clonal amplification, has a higher probability of accumulating somatic gene mutations.

Certain somatic gene mutations occur and are detectable in lymphocytes. For example, 6-thioguanine resistant ($TG^r$) T-lymphocytes result from mutation of the gene for hypoxanthine-guanine phosphoribosyltransferase (HPRT, hprt gene). These mutations can be detected by one of two methods, a short term autoradiographic assay and a more definitive clonal assay. Both are presently used for human mutagenicity monitoring. The clonal assay involves the isolation of in vivo-derived hprt mutant cells and their in vitro propagation in large populations for full characterization. Such human somatic mutant cells have been characterized and shown to maintain the $TG^r$ phenotype in vitro in the absence of selection and to be deficient in HPRT activity. Furthermore, in vivo-derived mutants show hprt gene structural alterations as defined by Southern blots probed with a cDNA hprt probe. Both assays are based on the fact that cells exhibiting the mutation termed hprt$^-$ are able to survive in the presence of 6-thioguanine, whereas wild-type cells having the hprt$^+$ genotype are killed.

TCR gene rearrangement patterns can also be defined for wild type and hprt mutant T-cell clones isolated in clonal assays. As expected on the basis of the large repertoire of possible TCR patterns, most independently isolated wild-type clones show unique TCR gene rearrangement patterns when studied by Southern blots and probed with the $\alpha$, $\beta$ or $\gamma$ TCR gene probes. However, studies of TCR gene rearrangement patterns among spontaneously arising hprt$^-$ mutant colonies show that clonal amplification of varying degrees has often occurred in vivo for clones that produce the mutants. This phenomenon of clonal amplification, as defined by replicate isolates of clones showing the same TCR gene rearrangement pattern, is most easily recognized in individuals who have hprt$^-$ T-cell mutant frequencies greater than $50 \times 10^{-6}$ when the "normal" spontaneous mutant frequency value is approximately $5 \times 10^{-6}$. Spontaneous somatic gene mutation in vivo in human T-lymphocytes appears to occur preferentially in those T-lymphocytes that are either actively dividing in vivo or have recently undergone division in vivo. In either case, mutation appears to mark cells derived from clones that are undergoing clonal amplification. By directing attention to only the mutant fraction of lymphocytes obtained from a sample, which should be representative of the total in vivo T-lymphocyte population, the present method permits more effective identification of the small minority subpopulation of cells that are undergoing clonal amplification in vivo. By first isolating that fraction of the sampled lymphocytes which exhibit somatic mutations, the subfraction exhibiting clonal amplification may be more readily detected. When correlated with clinical or other information, this method serves to identify cells undergoing cell amplification in response to antigen stimulus of some biologic or pathologic importance to the host.

A clonal assay to define hprt$^-$ gene mutants in lymphocytes is therefore useful in providing a method to identify, study and produce cells that are representatives of clones that have undergone clonal amplification in vivo. Cells are isolated in clonal assays, propagated into large populations, and characterized. Characterization includes study of the DNA by Southern blots with suitable T-cell receptor gene probes. The present invention provides such a method for determining clonal lymphocyte amplification in a mammal.

The method of the invention requires a sample of mature lymphocytes from the individual, for example obtained from a sample of body fluid. Preferably, this body fluid is whole blood obtained by venipuncture. An anticoagulant, such as heparin, is combined with the blood sample to prevent clotting. Alternatively, other appropriate body fluids containing mature lymphocytes such as synovial fluid, pleural or peritoneal fluid, spinal fluid or others may be used. Lymphocytes are separated from the body fluid, preferably by a Ficoll-Hypaque density gradient centrifugation, although other appropriate methods may be employed. The lymphocytes so obtained are washed, preferably with isotonic saline, and transferred to tissue culture medium, such as RPMI-1640, or other appropriate medium. Preferably, the medium contains a nutrient source, such as serum. In addition, an agent such as a mitogen may be added to activate or "prime" the cells. Preferably, phytohemagglutinin (PHA) is the priming agent. Other appropriate priming agents include lectins such as concanavalin-A (CON-A) or Poke Weed Mitogen (PWM). Each of these priming agents activates different subpopulations of lymphocytes. It is also possible to prime or activate T-lymphocytes using an anti-T3 antibody. Lymphocytes are preferably primed or activated for 24 to 48 hours. This interval is chosen so that cell division does not occur in vitro. Cell division at this stage is undesirable in that it provides a propitious opportunity for new mutation events to occur.

Lymphocytes are removed from the culture medium, washed and replated in appropriate medium at an appropriate dilution. The primed cells are then inoculated into the wells of microtiter plates in very small volumes in limiting dilutions. The total inoculum in each well includes appropriate medium, a nutrient source, and, preferably, inactivated feeder cells, a growth factor, such as a T-cell growth factor (TCGF) for T-cells or a B-cell growth factor (BCGF) for B-cells. These limiting dilutions inocula are selected to contain either 0.5, 1 or 2 cells per well, in those wells that are in plates to be used to determine cloning efficiency.

Wells in other plates used for determining the presence of mutation at a gene locus are inoculated with 1 to $2 \times 10^4$ cells per well in an inoculum medium as above which also includes an indicator agent. For example, 6-thioguanine can be used to determine whether cells have the wild-type hprt+ allele or a mutant hprt− allele. Cells with the wild-type allele do not survive in the presence of 6-thioguanine, while those cells with the mutant genotype can survive. The hprt− allele is extremely rare in natural cell populations. Growth of cell colonies in the presence of this indicator agent therefore indicates that a prior mutation event has occurred within the cell line. Other indicators can be used, however, including 8-azaguanine which can detect mutations at the hprt locus, and 6-mercaptopurine which can also detect mutations at the hprt locus. 8-azaguanine provides less stringent selection than 6-thioguanine, however, thus altering the frequency and profile of mutant cells obtained. Other possible indicators include diphtheria toxin, Ouabain, anti-HLA antibodies and complement, which detect mutations in the diphtheria-resistance, Oubain-resistance and HLA genes, respectively.

The indicator agent need not necessarily kill cells of a particular genotype so long as it provides a mechanism to distinguish between wild-type and mutant genotypes. For example, the indicator could potentially bind to cells of a certain genotype, thereby allowing separation as by a cell sorter. Other mechanisms of distinguishing genotypes will be evident to those skilled in the art. Therefore, two sets of plates are prepared: those that include very low numbers of cells and no indicator agent and those that include larger number of cells in the presence of an indicator agent. The later plates are used to determine the mutuant fraction. The technical details of this limiting dilutant inoculation can be varied. For example, although preferably round bottom microliter wells are used, flat bottom wells may allow better outgrowth of cells. Although a variety of feeder cells can be used, X-irradiated B-lymphoblastoid cells are preferred.

The number of cells inoculated into the wells containing the indicator agent to determine mutant fractions is varied depending upon the anticipated mutant frequency. For example, if a high or elevated mutant frequency is expected, less than $10^4$ cells per well are inoculated, for example $10^3$. Duplicate plates, such as three or more each containing 96 microliter wells are inoculated with cells at low density to determine cloning efficiency. As large a number of plates as is practical is inoculated with a higher density of cells in the presence of the indicator agent.

Plates are placed in the incubator under standard conditions and the wells observed for growing clones. Usually, wells are inspected after 7, 10 and 14 days. The number of wells in each plate that contain growing cells are counted and the fraction of positive wells per plate determined. This fraction is simply the number of positive wells containing growing clones over the total number of wells. Cloning efficiencies are calculated for the low density cloning efficiency plates and the high density mutant fraction plates containing the indicator agent, such as 6-thioguanine. The cloning efficiencies are determined by the $P_O$ class of the Poisson distribution which is defined as $P_O = e^{-x}$ where x is the average number of cells that were capable of growth originally plated into the wells. x divided by inoculum size gives cloning efficiency (CE).

In essence, two cloning efficiencies are calculated for each experiment. A cloning efficiency can be determined both for cells growing without an indicator agent and for cells inoculated and growing in the presence of an indicator agent. The former is termed the cloning efficiency (CE) and the latter the mutant fraction (MF). The mutant frequency is then calculated as $$\frac{MF}{CE}.$$

Growing cells are transferred to progressively larger culture vessels to develop large populations of cloned cells. Once large cloned populations are developed, these can be characterized as desired. For example, cells can be phenotyped for cell surface markers, e.g., T4, T8, T11 and T3, etc. by standard and well-known techniques. The enzyme activity of HPRT can be determined in wild type and mutant clones to define the true loss of enzyme activity expected in the mutants. Chromosomal analysis can be performed on these clones. The DNA from the clones is analyzed by the Southern blot technique which is well-known to those skilled in the art. Briefly, DNA from clones is digested with restriction enzymes and the fragments separated, for example by electrophoresis. Appropriate gene probes are then contacted with the separated fragments in order to determine the pattern of the fragments. Many restriction enzymes and various probes can be used for this purpose. For example, the Southern blot can be probed using the cDNA hprt gene probe to define the structural changes that have occurred within the small hprt gene.

Other methods are available for detecting and characterizing mutations, such as nucleic acid sequencing, or RNAase cleavage. All of these permit to definition the changes and spectrum of changes that have occurred in the gene mutation.

The DNA restriction fragment patterns on the Southern blots from the wild type and mutant clones are also analyzed to determine the arrangement of the regions of nucleic acid encoding the T-cell receptor. Probes for either the $\alpha$, $\beta$ or $\gamma$TCR gene can be used. Southern blot analysis for TCR gene arrangement patterns is used to define independent clonality of wild type or hprt mutant clones. Preferably the $\beta$ gene probe is used, or alternatively the $\gamma$. For a complete study of T-cell receptor gene rearrangements, the cloned cell DNA should be restricted with two or more restriction enzymes or analyzed at two or more TCR genes. This repetition is particularly important in order to determine whether two, three or more clones share a particular TCR gene rearrangement pattern. It is the sharing of similar patterns among several mutant cloned populations that define whether those particular clones derive from cells that have undergone clonal amplification in vivo. The identification of many mutant clones that share the same TCR gene rearrangement patterns from a given individual serves to indicate a T-cell clone that has undergone amplification in that individual.

The present method may be modified for use with B-cells. Again, lymphocyte samples are obtained and separated as described. In this instance, however, priming or activation will require an anti-IgM or anti-C'3 B-receptor in order to activate or stimulate the cells prior to cloning. Cloning is performed preferably in the presence of a B-cell growth factor. The assay for hprt⁻ gene mutation for B-cells is performed as described herein for T-cells. The rearrangement patterns analyzed are the rearrangements of the regions of nucleic acid encoding the immunoglobulin peptides. Clonal amplifications are recognized in a manner similar to that described above.

As used herein, the term "lymphocyte-mediated pathology" refers to any condition in which an inappropriate lymphocyte response is a component of the pathology. While the normal immune system is closely regulated, aberrations in immune response are not uncommon. In some instances, the immune system functions inappropriately and reacts to a component of the host as if it were, in fact, foreign. Such a response results in an autoimmune disease, in which the host's immune system attacks the host's own tissue. In other instances, lymphocytes replicate inappropriately and without control. Such replication results in a cancerous condition known as a lymphoma.

T cells, as the primary regulators of the immune system, directly or indirectly effect such autoimmune pathologies. The term is intended to include both diseases directly mediated by T cells and those, such as myasthenia gravis, which are characterized primarily by damage resulting from antibody binding, but also reflect an inappropriate T cell response which contributes to the production of those antibodies.

Where the antigen to which an autoimmune response is known, the invention permits specific identification of lymphocyte clones involved in the autoimmune response. Once mutated cloned cell populations are isolated they can be tested for reactivity to the antigen in question. Alternatively, isolated cloned cell populations can be used to determine whether a preselected antigen is the target antigen of an immune response. The presence of isolated mutated cloned cell populations can be tested to determine whether they are reactive with such an antigen. For example, reactivity of clones, or a preponderance of the clones, with a particular suspected antigen is indicative of the antigen's role in the lymphocyte mediated pathologic state. In some instances it is necessary to test multiple clones or clones from multiple individuals for such reactivity.

Other features and advantages of the present invention will become apparent from the following, more detailed Examples which illustrate, by way of example, the principles of the invention.

EXAMPLE I

CLONING OF T-LYMPHOCYTES

T-cell lymphocytes were cloned according to the method of O'Neill, et al. (1987), Mutagenesis 2:87, which is incorporated herein by reference.

Human peripheral blood samples were obtained by venipuncture and heparinized within 10 units/ml whole blood beef lung heparin (Upjohn, Washington, D.C.). The samples were overlaid into sterile 50 ml centrifuge tubes (Corning Glass Co., Corning, N.Y.) containing Ficoll (m.w. 400,000)-Hypaque-M, 90% (specific gravity 1.077) (Ficoll obtained from Sigma Chemical Co., St. Louis, Mo.; Hypaque obtained from Sterling Drug [Winthrop], New York, N.Y.) at a ratio of 2:1 whole blood to Ficoll-Hypaque. The sample-containing tubes were centrifuged at 600xG for 30 minutes at 20° C. The mononuclear cell fractions, represented by the white band at the plasma-Ficoll-Hypaque interface, were transferred to fresh tubes, and washed twice with phosphate buffered saline (PBS). The "basic medium" employed was RPMI 1640 containing 25 MM HEPES buffer, 2 mM L-glutamine, 100 units/ml penicillin and 100 μg/ml streptomycin sulfate which was adjusted to pH 7.2 before the addition of 2 g/l sodium bicarbonate. All lymphocyte cultures were in basic medium containing 20% nutrient medium HL-1 (Ventrex Laboratories, Portland, Me.). For cryopreservation, cells were frozen at $-1°$ C./min in basic medium to which was added 20% fetal bovine serum (FBS; Hyclone, Salt Lake City, Utah) and 7.5% dimethyl sulfoxide (DMSO; VWR Scientific, Rochester, N.Y.) and stored under liquid nitrogen.

T-lymphocytes were cloned as follows. Fresh, single donor mononuclear cells were initially "primed" by culturing $1 \times 10^6$ mononuclear cells/ml in growth medium containing 15% FBS and 1 μg/ml phytohemagglutinin-M (PHA-M; Wellcome Diagnostics, Greensville, S.C.) for 36 hours. The cell suspensions were then centrifuged at $500 \times g$ for 10 minutes.

Cells were inoculated into microtiter plates in two sets. In order to determine cloning efficiency (CE), a sample volume of cell suspension equivalent to 1 to 2 cells/well was placed in individual wells of 96-well microliter plates. To one set of wells was added growth medium containing 15% FBS and an optimal amount of TCGF, determined as described below and $5 \times 10^3$ feeder cells, to a final volume of 0.2 ml/well. The feeder cells used were mycoplasma-free, hprt⁻ derivatives of WI-L2 lymphoblastoid cells designated TK6 and grown in medium RPMI 1640 containing 10% horse serum and no antibiotics. The TK6 cells had been previously irradiated on dry ice with a cobalt 60 source at 150 rad/minute, for a total irradiation of 10 krad. Parallel sets of plates were inoculated with about $10^4$ cells/well in 0.2 ml growth medium to which 10 μM 6-thioguanine (Sigma Chemical Co., St. Louis, Mo.) and $5 \times 10^3$ feeder cells were added. Cells that survive in the selection medium have had a mutation event at the hprt locus, and are termed TG$^r$ mutants.

The plates were then incubated, without change of medium, for 14 days to permit colony growth. The wells were monitored for colony growth by use of an inverted phase contrast microscope. Each plate was scored for cell growth by two individuals on days 7, 10 and 14.

The TCGF used was the conditioned medium from PHA-stimulated human peripheral blood lymphocytes prepared essentially as described by Inouye et al. (1980), Scand. J. Immunol. 12:149. Briefly, irradiated (1000 rad) human mononuclear cells from several individuals were inoculated at a density of 1 to $2 \times 10^6$ cells/ml in medium RPMI 1640 containing 1% FBS, 1 µg/ml phytohemagglutinin (PHA; HA-17 m Wellcome Diagnostics, Greenville, S.C.) and $2 \times 10^5$ irradiated (4000 rad) TK6 cells/ml. After 42 hours incubation, the supernatants were collected, pooled, filtered and frozen at $-30°$ C. Three different assays were employed for testing the TCGF activity to define the optimal amount for T-cell growth. The first assay employed was a short-term culture which measures tritiated thymidine ($^3$H-dT) incorporation with growth factor dependent T-lymphocytes. The T-lymphocytes employed in this assay had been grown in vitro for at least 14 days and were no longer responsive to PHA. The cells were plated at $2 \times 10^4$ cells per microliter well (96-well, flat bottom) in 200 µl of medium containing the designated amount of TCGF, incubated for 24 hours and 1 µCi$^3$H-dT added (spec. activ. $-6$ Ci/mmol) and incubated for an additional 24 hours. The incorporation of radioactivity was determined by the use of a cell harvester and a liquid scintillation spectrometer. The second assay was performed as described below with cells incubated with 1 µg/ml PHA for 40 hours and then plated at 1 or 2 cells/round-bottom well in different amounts of TCGF. The third assay was a mass culture growth with the same cells plated in a cloning assay. The cells were plated in 2-cm$^2$ wells at $1 \times 10^4$ cells/well in 2 ml of medium containing $2 \times 10^5$ irradiated TK6 cells and different amounts of TCGF. Cell number was determined by the use of a Coulter Counter. The maximum cell number (usually attained after 7-9 days incubation) was used as the measure of TCGF activity. TCGF was used to produce maximum cell growth and cloning as determined by testing, usually 20% TCGF. Alternatively, commercial TCGF (human T-cell polyclone; Collaborative Research Inc., Cambridge, Mass.) can be used at 5 or 10% TCGF. Other sources of growth factor are recombinant Il-2 or the supernatant of ex-vivo activated lymphokine-activated killer cells which contain recombinant Il-2 (LAK-Sup).

The cloning efficiency (CE) in non-selection medium and the mutant fraction (MF) in selection medium are calculated by the Poisson relationship $P_O = e^{-x}$, which defines x as the average number of clonable cells/well. The value of x divided by the number of cells added to each well defines the cloning efficiency (CE) and the mutant fraction (MF), respectively. The mutant fraction divided by the cloning efficiency (CE) yields the measured mutant frequency (MF).

Cells from the clones were grown and expanded in vitro to characterize the T-lymphocyte colonies. The modified RPMI 1640 medium containing optimal amounts of TCGF and $2.5 \times 10^5$ irradiated TK6 cells per cm$^2$ or surface area was used. The colonies in positive wells in microliter dishes contained $1 \times 10^4$ to $2 \times 10^5$ cells after 10-14 days incubation. These cells were transferred to 2 cm wells containing 2 ml of medium (and 10 µM 6-thioguanine for selected colonies) and incubated until the surface of the well is 70 to 80% confluent, usually in 3 to 6 days. The cells were then removed and centrifuged at $500 \times 6$ for 10 minutes to remove the depleted medium and transferred to three 4 cm$^2$ wells in 4 ml of medium at about $1 \times 10^5$ cells per ml. Under the above conditions, population doubling times were 18 to 22 hours and the cells were subcultured at 4 day intervals at $1 \cdot 10^3$ cells/ml when cell densities of 1 to $1.5 \times 10^6$ cells/ml were attained.

EXAMPLE II

CHARACTERIZATION OF T-CELL MUTANTS

In order to demonstrate that T-cells have been cloned, and that the TG$^r$ cells are mutants, some growing clones were characterized for T-cell surface markers and HPRT activity. The nature of the hprt gene change was determined in mutants by Southern blot analysis.

Surface antigens on cells of individual clones were detected and characterized using mouse monoclonal antibodies against $T_3$, $T_{11}$, $T_4$ and $T_8$ (Ortho Diagnostics, Raritan, N.J.), followed by goat anti-mouse fluorescein-isothiocynatelabelled antibodies (Monoclonal Antibodies, Inc., Mountain View, Calif.). Cells were scored by fluorescence microscopy for surface markers $T_3$, $T_{11}$, $T_4$ and $T_8$.

HPRT enzyme activity was assayed according to the method of DeMars and Held (1972), Humangenetik 96:87, modified as follows. T-lymphocytes (approximately $2 \times 10^6$), were washed twice with 0.15M KCl and suspended in 100 µl to 200 µl cold 0.01M Tris buffer, pH 7.4 and were disrupted by sonication. Following centrifugation for 30 seconds in a microfuge, diluted supernatants were added to reaction mixtures containing 0.1M Tris buffer, pH 8.4; $5 \times 10^{-2}$M MgSO$_4$; $1.9 \times 10^{-3}$M hypoxanthine; $10^{-4}$M $^{14}$C hypoxanthine 5 µC/ml., $10^{-2}$M 5-phosphoribosyl 1-pyrophosphate, and distilled water. The reaction was stopped with 4M formic acid after 2 hours incubation in a $37°$ C. water bath. Enzymatic conversion of hypoxanthine (H) to inosine (I) and inosinic acid (IMP) was determined by liquid scintillation counting of Whatman 3 MM paper spots after ascending chromatography of the reaction mixture in 5% Na$_2$HPO4. Conversion was calculated as:

$$\% \text{ Conversion} = \frac{\text{cpm} + \text{cmp } IMP}{\text{cmp } H + \text{CPM } I + \text{cpm } IMP} \times 100$$

The protein content of cell extracts was determined by a modification of the Lowry procedure.

In order to determine structural alterations with the hprt gene T-cell receptors for the mutant cloned lymphocyte populations derived through the method of Example I, the DNA encoding hprt was isolated and characterized. Southern blot analysis was performed according to the method of Albertini et al., (1985), Nature 316:369, which is incorporated herein by reference. Genomic DNA was isolated from selected wild type and TG$^r$ mutant colonies.

To isolate the DNA, 15 to $20 \times 10^6$ frozen cells for each colony were washed and resuspended in 1 ml T$_{10}$E$_1$ (10 mM Tris, 1 mM EDTA pH 8.0). Four ml TENS (25 mM Tris-HCl pH 8, 100 mM NaCl, 10 mM EDTA, 0.6% SDS) were added and the solution was heated to $65°$ C. for 15 minutes. Proteinase K (0.5 mg) was added, and the mixture incubated overnight at $37°$ C. An additional 0.14 mg of proteinase K was added and digestion continued for 3 hours. The resulting solution was pheno-extracted twice, followed by three chloroform/isoamyl alcohol (24:1) extractions, precipitated in ethanol and resuspended in T$_{10}$E$_1$. For the Southern blots, about 7.5 μg per lane of genomic DNA was digested with restriction enzymes (Pst-1, HindIII or alternatively, BamHI), fractionated on a 0.7% agarose gel in TAE buffer (40 mM Tris-acetate, 2 mM EDTA) and transferred to nitrocellulose filters (Schleicher and Schuell, Keene, N.H.). Pre-hybridization was performed for 5 hours at 42° C. in 40 ml of 50% Formamide, 5X SSC, 5X Denhardt's 50 mM Tris pH 7.5, with 250 μg/ml sheared and denatured salmon sperm DNA (Sigma Chemical Co., St. Louis, Mo.). The material was hybridized overnight at 42° C. in 20 ml of 50% formamide, 5X SSC, 1X Denhardt's 20 mM Tris pH 7.5, 10% dextran sulfate with 250 mg/ml sheared and denatured salmon sperm DNA and $1.0-1.5 \times 10^6$ cpm/ml of labelled cDNA probe.

The hprt probe is the Pst I insert from pHPT 30 or, alternatively pHPT 31 (Brennand et al., 1983, J. Biol. Chem. 258:9593), a 947 bp cDNA probe containing the complete hprt coding sequence. For some blots, a MsoI - PstI subfragment of the entire probe was used to reduce background. (MspI o removes the 5' end of the probe which includes most of exon 1).

After hybridization, hprt blots were washed for 15 minutes in 2X SSC, 0.5% SDS at room temperature, then for 30 minutes in 2X SSC, 0.19% SDS at 57° C. and finally, twice for 30 minutes in 0.1X SSSC, 0.1% SDS at 57° C. Washing of the TCR $\beta$ and $\gamma$ blots consisted of three 5 minute washes in 2X SSC, 0.2% SDS at 65°. Autoradiography was performed at −80° C. with Kodak XAR-5 film (Kodak, Rochester, N.Y.) and Dupont Lighting plus screens (E. I. Dupont de Nemours, Wilmington, Del.), for 3-5 days. Interpretations of the hprt gene alterations were based on the assignments of exons to restriction fragments made by Patel et al., (1984), Som. Cell. Molec. Gen. 10:483, and Yang et al., (1984), Nature 310:412, both of which are incorporated herein by reference.

EXAMPLE III

DETERMINATION OF T-CELL RECEPTOR GENE REARRANGEMENTS

The rearrangement of the regions of DNA encoding the TCRs were determined for populations of hprt mutant cells. The gene filters used in Example II were reused for this purpose. For rescue of filters, probe was removed from the nitrocellulose by two 15-minute washes in distilled water at 65° C. The filter was then placed in 40 ml of the prehybridization solution and refrigerated until ready for additional hybridization.

Therefore, the DNA on the filter was that prepared as described in Example II. The DNA encoding the T-cell receptors was contained in this DNA and was analyzed by probing with the $\alpha$, $\beta$ and $\gamma$ TCR probes by the method described in Example II, using these probes in place of those therein described. The TCR probe used was pY1.4 (Yanagi, et site of PUC8, although other TCR probes can also be used. The TCR $\beta$ probe used is the insert from Jurkat 2 (Yanagi et al.; (1984), Nature 308:145) containing nucleotides 100 to 870 cloned into the Pst I site of pBR322. The T$\gamma$ probe used is the 700 bp HindIII - EcoRI insert pH60 (Lefranc et al., (1986), Nature 319:420), a genomic clone containing J $\gamma$1.

EXAMPLE IV

DETERMINATION OF CLONAL AMPLIFICATION

In order to determine whether the various clones studied were derived from independent mutation events or from a single mutation event in a common parental cell, patterns of gene structure of T-cell receptors were compared. When similar Southern blot patterns were found, which resulted from (1) cleavage with two separate restriction enzymes or (2) hybridization with separate probes, the T-cell receptors were considered similar so as to indicate that they reflected a single prior rearrangement in a common parent. Such similarity indicated that a clonal amplification event occurred to yield the mutants as isolated.

For example, a blood sample from an adult female was used to clone and characterize T-lymphocytes by the methods set forth in Examples I to III, above. The mutant frequency values obtained were as high as $500 \times 10^6$ Southern blot patterns were obtained from HindIII-digested DNA obtained from these samples to study a total of 51 TG$^r$ mutant colonies. However, among these 51 TG$^r$ mutant colonies, 47 colonies showed similar T-cell receptor $\beta$ gene rearrangement patterns, thus demonstrating clonal amplification in this individual. A large subset of these mutant colonies were studied for TCR $\gamma$ gene patterns, and these patterns were also similar in the mutants.

Lymphocytes cloned from an adult male with mutant T-cell clones studied had similar TCR gene rearrangement patterns when probed with the $\beta$ or $\gamma$ TCR gene probes. A second smaller group of 3 mutant clones exhibited a different but related TCR pattern when probed with the $\beta$ and $\gamma$ gene probes, suggesting that at least two clones were amplifying in this individual.

EXAMPLE V

CLONING OF B-LYMPHOCYTES

B-lymphocyte mutant clones are obtained according to the methods of Example I, with the following modifications. The cells are "primed" with anti-IgM antibodies or anti-C'3B receptor antibodies. The cells are grown in growth medium to which is added B-Cell Growth Factor or are infected with Epstein Barr virus to achieve continuous proliferation. The nucleic acids encoding IgG genes are characterized according to the method of Example III, with probes specific to the C, V, D or J domains in order to identify gene rearrangement patterns.

Example VI

ISOLATION OF HUMAN MYELIN BASIC PROTEIN-REACTIVE T CELL CLONES a. Patient Samples

Peripheral blood samples were obtained on patients from the MS clinic at the Medical Center Hospital of Vermont. Most patients had been receiving low dose steroid therapy up to the time of sampling. Patients receiving cyclophosphamide were excluded. One patient had been on Imuran before analysis.

b. T Cell Cloning

Cloning was performed as described by O'Neill et al., Mutagenesis 2:87-94 (1987). Briefly, mononuclear cells were obtained from peripheral blood after separation with Sepracell (Sepratech, Oklahoma City, Okla.) and either cultured immediately or cryopreserved. Mononuclear cells were diluted to $1 \times 10^6$ cells/ml and incubated with 1 μg/ml PHA. After 36-40 hours, the cells were then centrifuged, resuspended and counted. Cells were inoculated at 1, 2, and 10 cells/well (nonselection) or $5 \times 10^3$ to $2 \times 10^4$ cells/well (selection) in 96 well round bottom microliter plates. Growth medium consisted of modified RPMI 1640 medium containing 10% fetal bovine serum (FBS), 20% HL-1 medium (Ventrex), 25 mM HEPES, 2 mM L-glutamine, and optimal amounts of T cell growth factor (TCGF). Growth factor preparations were obtained as a byproduct of a lymphokine-activated killer/interleukin-2 clinical trial underway at the Medical Center Hospital of Vermont. Selection wells contained $10^{-5}$M Thioguanine (TG). Wells also contained $5 \times 10^{-3}$ irradiated (9000 rad) TK6 lymphoblastoid feeder cells, a hprt$^-$ derivative of the WIL-2 cell line, all in a total volume of 0.2 ml. Cells were incubated for 10-14 days and scored for colony growth by use of an inverted phase microscope.

c. Mass Culture Selection

Peripheral blood mononuclear cells isolated and washed after separation on Sepracell were cultured with 10% FCS, 20% HL-1, 20% TCGF, and 1 μg/ml PHA. Both selection and nonselection cultures were cultured at $1 \times 10^6$ cells/ml. Selection cultures were started as a 5 ml culture in a T-75 flask, with $10^{-5}$M TG. Cultures were checked after 4 days for growth, and RPMI 1640 media containing 20% HL-1, 10% FCS, 20% TCGF was added to obtain a density of $2 \times 10^5$ cells/ml. Selection cultures were either centrifuged and resuspended in the same volume of fresh media or centrifuged over a Ficoll/Hypaque gradient to eliminate cellular debris. The viable cells were then washed with RPMI and resuspended at $2 \times 10^{-5}$ cells/ml in fresh growth medium. Once $25 \times 10^6$ cells were obtained from a given culture, $20 \times 10^6$ cells were centrifuged and resuspended in $T_{10}E_1$ for isolation of genomic DNA, the remaining cells were resuspended and cryopreserved for further analysis.

d. Isolation of Human Basic Protein (HBP)

HBP was isolated according to the method of Oshiro and Eylar, Archives of Biochemistry and Biophysics 138:392-396 (1970) as modified by Brostoff and Mason, J. of Immunology 133:1938 (1984), both of which are incorporated herein by reference.

Briefly, approximately 350 g of human brain white matter was homogenized in 700 ml methanol for 2 minutes in a Waring commercial blender (model No. 34BL22) (Waring, New Hartford, Conn.) followed by the addition of 1400 ml of chloroform and additional blending in a Waring commercial blender for 4 minutes. The homogenate was allowed to separate in a separating funnel for two hours. The lower plasma was discarded and the upper phase mixed with celite (Manville Products, Denver, Colo.) until it reached the consistency of a milkshake. The celite mixture was filtered on a Buchner funnel through Whatman #1 filter paper (Whatman Ltd., England) and washed with 200 ml acetone. The celite mixture was removed and suspended in 3.2 L of distilled water adjusted to pH 1.9 with concentrated hydrochloric acid. After stirring for 18 hours, the material was centrifuged at 10,000 ×g for 15 minutes, the residue discarded and the supernatant adjusted to pH 7.0 with concentrated ammonium hydroxide. The solution was stirred for 1 hour and filtered through Whatman No. 1 filter paper. Ammonium sulfate (350 g/liter) was added to the filtrate which was then adjusted to pH 7.0 with ammonium hydroxide, stirred for 1 hour, and centrifuged at 10,000 ×g for 15 minutes. The pellet was resuspended in 200 ml distilled water and dialyzed overnight in Spectrapor (Spectrum Medical Industries, Los Angeles, Calif.) dialysis tubing (MW cutoff 3500) against 4 changes of 2 liters of distilled water. The precipitate after dialysis was removed by centrifugation at 10,000 ×g for 15 minutes. Ammonium acetate was added to the supernatant to bring the concentration to 0.3M before loading onto a column of Cellex P (Bio-Rad Laboratories, Richmond, Calif.) equilibrated with 0.3 ammonium acetate pH 7.0. The Cellex P column (9×2.5 cm, flow rate 2.5 ml/min) was washed successively with 0.2M and 0.5M ammonium acetate and the basic protein eluted in 1.0M ammonium acetate and identified by its optical density at 280 nm. It was dialyzed as above and lyophilized prior to use. All operations were carried out at 4° C. unless otherwise noted.

e. Proliferation to Human Basic Protein

T-cell clones were tested for reactivity to human basic protein (HBP) as described in Richert et al., Neurology, 38:739-742 (1988), which is incorporated herein by reference. Briefly, $10^4$ cloned cells were placed with $2.5 \times 10^4$ irradiated (3000 rad) autologous PBMCs in flat-bottomed 96-well microliter plates. Wells received either optimal concentrations of recombinant IL2 and 0.1 μg/ml PHA, or media as + and − controls, respectively. Basic protein was tested at 3 serial log doses (1, 10, and 100 μg/ml or 3, 30, and 300 μg/ml), each was tested in triplicate in 0.2 ml volumes. After 54 hours, cultures were pulsed with 1 μCi/well $^3$H-thymidine for 16 hours before harvesting on a multi-channel automated sample harvester. Thymidine incorporation was measured in a scintillation counter and data expressed as the mean ± standard deviation of the triplicates or stimulation index.

f. Proliferation to HTLV-1

T cell clones to be tested for reactivity to HTLV-1 virus were washed, resuspended, and plated at $10^4$ cells/well with $2.5 \times 10^4$ irradiated (3000 rad) autologous PBMC's. Controls were added as in the above assay for response to HBP, and virus was then added at 0.1, 1, and 10 μg/ml. After 54 hours, the wells were pulsed with $^3$H-thymidine (1 μCi/well) for the final 16 hours of culture. The wells were harvested and counted as described for response to HBP proliferation.

Patient reactivities are presented in Tables I through III. Stimulation index is CPM incorporated into cultures with antigen divided by cultures incubated without antigen. CPM of cultures without antigen averaged 814 CPM.

TABLE I

Patient #1

Response of clone M31 to human myelin basic protein (MBP) and HTLV-1

| CLONE | ANTIGEN (conc) | STIMULATION INDEX |
|---|---|---|
| M31 | MBP (100 µg/ml) | 2.3 |
| M31 | MBP (1.0 µg/ml) | 1.6 |
| M31 | MBP (0.1 µg/ml) | 2.8 |
| M31 | MBP (0.01 µg/ml) | 4.6 |
| M31 | HTLV-1 (3.3 µg/ml) | 4.4 |
| M31 | HTLV-1 (0.33 µg/ml) | 3.3 |
| M31 | HTLV-1 (0.033 µg/ml) | 1.9 |
| M31 | HTLV-1 (0.0033 µg/ml) | 1.2 |

TABLE II

Patient #2
Response of clone M14 and M37 to human myelin basic protein (HBP)

| | Antigen Concentration | Stimulation Index |
|---|---|---|
| Clone M14 | 300 µg/ml | 4.8 |
| Clone M14 | 30 µg/ml | 1.2 |
| Clone M14 | 3 µg/ml | 0.8 |
| Clone M37 | 300 µg/ml | 2.5 |
| Clone M37 | 30 µg/ml | 8.7 |
| Clone M37 | 3 µg/ml | 2.4 |

TABLE III

RESPONSE OF MUTANT CLONES FROM PATIENT #3 TO HUMAN MYELIN BASIC PROTEIN (100 µg/ml)

| CLONE # | STIMULATION INDEX |
|---|---|
| M12 | (4.92) |
| M13 | (6.22) |
| M18 | (9.30) |
| M26 | (4.94) |
| M27 | (4.89) |
| M31 | (7.53) |

Although the invention has been described with reference to the presently-preferred embodiment, it should be understood that various modifications can be made by those skilled in the art without departing from the invention. Accordingly, the invention is limited only by the following claims.

I claim:

1. A method for detecting clonal lymphocyte amplification in a mammal, comprising the steps of:
   (a) obtaining a sample of lymphocytes from said mammal;
   (b) cloning said lymphocytes in the presence of an agent indicative of a prior somatic mutation event at a gene locus in a lymphocyte, to produce cloned cell populations;
   (c) selecting those cloned cell populations that are indicated to have had said prior mutation event;
   (d) growing said selected cloned cell populations separately to provide isolated mutated cloned cell populations;
   (e) determining in said isolated mutated cloned cell populations the arrangement of the regions of the nucleic acid encoding an antigen receptor specific to a particular antigen;
   (f) comparing the arrangement of the regions of the nucleic acid encoding an antigen receptor specific to a particular antigen among the isolated mutated cloned cell populations; and
   (g) identifying cells undergoing amplification in response to a particular antigen stimulus, whereby the presence of a similar structure of the regions of nucleic acid encoding a specific antigen receptor in separate isolated mutated cell clones indicates clonal lymphocyte amplification in said mammal.

2. The method of claim 1 wherein said mammal is a human.

3. The method of claim 1 wherein said agent indicative of a prior mutation event is selected from the group consisting of 6-thioguanine, 8-azaguanine, 6 mercaptopurine, diphtheria toxin, Ouabain and anti-HLA antibodies and complement.

4. The method of claim 1 wherein said gene locus is selected from the group consisting of hprt, diphtheria toxin resistance, Ouabain resistance and HLA.

5. The method of claim 1 wherein said agent indicative of said prior mutation event at said gene locus permits the proliferation of cells having a mutation at the gene locus while inhibiting the proliferation of cells having a wild type allele at the gene locus.

6. The method of claim 1 wherein said specific antigen receptor is the T-cell receptor.

7. The method of claim 1 wherein said specific antigen receptor is an immunoglobulin.

8. The method of claim 1 further comprising providing a growth factor in said cloning step.

9. The method of claim 1 wherein said determining step further comprises detecting the arrangement of the regions of nucleic acid encoding an antigen receptor specific for a particular antigen by hybridization of oligonucleotide probes specific to said nucleic acid.

10. The method of claim 1 wherein said determining step further comprises digesting said nucleic acid with restriction enzymes to produce restriction fragments.

11. The method of claim 1 wherein said cloning step further comprises providing said lymphocytes with a priming agent.

12. The method of claim 1 wherein said cloning step further comprises cloning said lymphocytes in the presence of feeder cells.

13. A method of diagnosing pathological states in a mammal suspected of having such pathology characterized by clonal lymphocyte amplification, comprising the steps of:
   (a) obtaining a sample of lymphocytes from said mammal;
   (b) cloning said lymphocytes in the presence of an agent indicative of a prior somatic mutation event at a gene locus in a lymphocyte, to produce cloned cell populations;
   (c) selecting those cloned cell populations that are indicated to have had said prior mutation event;
   (d) growing said selected cloned cell populations separately to provide isolated mutated cloned cell populations;
   (e) determining in said isolated mutated cloned cell populations the arrangement of the regions of the nucleic acid encoding an antigen receptor specific for a particular antigen;
   (f) comparing the arrangement of the regions of the nucleic acid encoding an antigen receptor specific for a particular antigen among the isolated mutated cloned cell populations; and
   (g) identifying cells undergoing amplification in response to a particular antigen stimulus, whereby the presence of a similar structure of the regions of nucleic acid encoding a specific antigen receptor in separate isolated mutated cell clones indicates clonal lymphocyte amplification indicative of said pathological state in said mammal.

14. A method for detecting clonal T-lymphocyte amplification in a mammal, comprising the steps of:
   (a) obtaining a sample of T-lymphocytes from said mammal;
   (b) cloning said T-lymphocytes in the presence of an agent indicative of a prior somatic mutation event at a gene locus in a lymphocyte, to produce cloned cell populations;
   (c) selecting those cloned cell populations that are indicated to have had said prior mutation event;
   (d) growing said selected cloned cell populations separately to provide isolated mutated cloned cell populations;
   (e) determining in said isolated mutated cloned cell populations the arrangement of the regions of the nucleic acid encoding an antigen receptor specific to a particular antigen;
   (f) comparing the arrangement of the regions of the nucleic acid encoding an antigen receptor specific to a particular antigen among the isolated mutated cloned cell populations; and
   (g) identifying cells undergoing amplification in response to a particular antigen stimulus, whereby the presence of a similar structure of the regions of nucleic acid encoding a specific antigen receptor in separate isolated mutated cell clones indicates clonal lymphocyte amplification in said mammal.

15. A method for identifying lymphocytes involved in a lymphocyte mediated pathologic state in a mammal comprising the steps of:
   (a) obtaining a sample of lymphocytes from said mammal;
   (b) cloning said lymphocytes in the presence of an agent indicative of a prior mutation event at a gene locus in a lymphocyte, to produce cloned cell populations;
   (c) selecting those cloned cell populations that are indicated to have had a prior mutation event;
   (d) growing said selected cloned cell populations separately to provide isolated mutated cloned cell populations;
   (e) testing the reactivity of said isolated mutated cloned cell populations to antigens suspected of causing said lymphocyte mediated pathologic state.

* * * * *

UNITED STATES PATENT AND TRADEMARK OFFICE
CERTIFICATE OF CORRECTION

PATENT NO. : 5,112,735
DATED : May 12, 1992
INVENTOR(S) : Richard J. Albertini

It is certified that error appears in the above-indentified patent and that said Letters Patent is hereby corrected as shown below:

Column 1, insert before the first paragraph: --The invention was supported in part by Grant No. NCI 5-R01-CA30688-08. The Government may have certain rights in the invention.--.

Column 2, lines 46-47, please delete "coding" and replace therefore --encoding--.

Column 10, line 3, please delete "1.·10$^3$" and replace therefore --1X10$^3$--.

Column 11, line 20, please delete "MsoI" and replace therefore --MspI--.

Column 11, line 22, please delete the "o" that precedes the word removes.

Column 11, line 60, please insert after Yanagi, et --al., (1984) PNAS 82:3430, a cDNA probe cloned into the EcoRI--.

Column 14, line 31, please delete "104" and replace therefore --10$^4$--.

UNITED STATES PATENT AND TRADEMARK OFFICE
CERTIFICATE OF CORRECTION

PATENT NO. : 5,112,735
DATED : May 12, 1992
INVENTOR(S) : Richard J. Albertini

It is certified that error appears in the above-indentified patent and that said Letters Patent is hereby corrected as shown below:

Column 14, line 50, please delete "104" and replace therefore --$10^4$--.

Column 15, line 53 (claim 1(c)), after the word prior, please insert therefore --somatic--.

Column 15, line 67 (claim 1(g)), after the words regions of, please insert therefore --the--.

Column 18, line 18, after the word populations; please insert therefore --and--.

Signed and Sealed this

Twelfth Day of July, 1994

Attest:

BRUCE LEHMAN

Attesting Officer  Commissioner of Patents and Trademarks